(12) United States Patent
Jin et al.

(10) Patent No.: US 6,783,810 B2
(45) Date of Patent: Aug. 31, 2004

(54) REDUCING POLYMERIZATION STRESS BY CONTROLLED SEGMENTAL CURING

(75) Inventors: Xiaoming Jin, Dover, DE (US); Paul D. Hammesfahr, Wyoming, DE (US)

(73) Assignee: Dentsply Research & Development Corp.

( * ) Notice: Subject to any disclaimer, the term of this patent is extended or adjusted under 35 U.S.C. 154(b) by 0 days.

(21) Appl. No.: 09/809,606

(22) Filed: Mar. 15, 2001

(65) Prior Publication Data

US 2002/0016378 A1 Feb. 7, 2002

Related U.S. Application Data

(60) Provisional application No. 60/189,614, filed on Mar. 15, 2000.

(51) Int. Cl.[7] .................................................. C08F 4/46
(52) U.S. Cl. ...................... 427/510; 427/487; 427/517; 427/508; 522/4; 522/1; 522/908; 433/229; 433/215; 433/217.1; 433/226; 523/116
(58) Field of Search ............................... 522/4, 1, 908; 433/29; 427/496, 508, 510, 517, 492, 493; 523/116

(56) References Cited

U.S. PATENT DOCUMENTS

| | | | |
|---|---|---|---|
| 4,332,439 A | 6/1982 | Lubbers et al. | 350/320 |
| 4,385,344 A | 5/1983 | Gonser | 362/32 |
| 4,491,453 A | 1/1985 | Koblitz et al. | 433/217 |
| 4,514,174 A | 4/1985 | Dougherty et al. | 433/226 |
| 5,110,513 A | 5/1992 | Puvilland | 264/19 |
| 5,229,230 A | 7/1993 | Kamon | 430/1 |
| 5,290,169 A | 3/1994 | Friedman et al. | 433/29 |
| 5,468,577 A | 11/1995 | France et al. | 514/562 |
| 5,472,991 A | 12/1995 | Schmitt et al. | 522/4 |
| 5,521,392 A | 5/1996 | Kennedy et al. | 250/492.1 |
| 5,634,711 A | 6/1997 | Kennedy et al. | 362/119 |
| 5,726,730 A | 3/1998 | Crawford et al. | 349/196 |
| 5,835,661 A | 11/1998 | Tai et al. | 285/146 |
| 5,879,159 A | 3/1999 | Cipolla | 433/29 |
| 5,912,470 A | 6/1999 | Eibofner et al. | 250/504 |
| 5,975,895 A | 11/1999 | Sullivan | 433/29 |
| 6,008,264 A | 12/1999 | Ostler et al. | 522/4 |
| 6,033,223 A | 3/2000 | Narusawaet et al. | 433/226 |
| 6,079,861 A | 6/2000 | Woodward et al. | 362/552 |

FOREIGN PATENT DOCUMENTS

| | | |
|---|---|---|
| CH | 244 401 | 9/1946 |
| DE | 198 03 302 | 8/1999 |
| EP | 0 875 360 | 11/1998 |
| WO | 00/67048 | 11/2000 |

*Primary Examiner*—James J. Seidleck
(74) *Attorney, Agent, or Firm*—Douglas J. Hura; James B. Bieber

(57) ABSTRACT

A photopolymerizable material is exposed to light to effect curing. A portion of the material is exposed to light in a conventional manner, while at least one other portion of the material is masked from direct exposure to the light by use of a mask (10) having at least one mask segment (11) which either completely or at least partially blocks the light. In this manner, the polymerization stress associated with the cured materials is limited or minimized due to extended molecular relaxation promoted by this controlled or hybrid curing technique. Also according to the invention, different segments (30, 31) of a material to be cured (22) are exposed to different wavelengths of light energy (21) or one such segment (30, 31) is exposed to light energy while another such segment is not.

1 Claim, 3 Drawing Sheets

REDUCING POLYMERIZATION STRESS BY CONTROLLED SEGMENTAL CURING

This application claims the benefit of Provisional Application No. 60/189,614, filed Mar. 15, 2000.

TECHNICAL FIELD

This invention relates to a method or technique to cure a polymerizable material with various light sources, particularly light curable materials that are selectively cured using special patterns. The patterns are either placed onto a special mask on the materials or onto the curing light tip, or by employing a special light source. As a result from such a segmental curing technique, the polymerization stress associated with the cured materials is limited or minimized due to extended molecular relaxation promoted by this controlled hybrid curing technique.

BACKGROUND OF THE INVENTION

Light cured materials are well known in the art. For example, it is known in the dental industry to place curable materials into place on a tooth or other dentition to be restored. The materials are then expose to light to effect curing. It has been found that a problem with some such materials is excessive shrinking during the polymerization or cure process.

In the past, many efforts have been made to reduce polymerization shrinkage because it was believed that the lower polymerization shrinkage would always lead to the lower polymerization stress. This is not always correct. For example, rapid polymerization using high powered light indeed resulted in lower polymerization shrinkage for some materials, but was also accompanied by increasing polymerization stresses that could not be relived due to the rapid cross-linked, rigid polymer network developed during fast curing. Recently, it has been understood that it is the polymerization stress that plays a most critical role in determining a successful dental restoration. Therefore, in attempts to reduce stress, various techniques have been explored, including changing the light intensity during curing, changing the spectrum of light distribution, and modulating the curing frequency et al, in addition to new resin development. It should be pointed out that there is one thing in common for all these approaches: one mass of chemically homogenous material is exposed to a relatively homogenous light source resulting in a relatively homogenous curing rate throughout the material.

Light with a defined wavelength can provide proper energy to activate a light curable material and to start polymerization leading a network formation. Such lights used for curing include, for example, visible light and UV light in terms of different frequency or wavelength; there are halogen light, LED light, plasma ARC light, and laser light in terms of different energy. In addition, different light structures, including lamp, filter, light guide have been used in order to change the light output by tuning both spectra and energy distribution. Unless otherwise noted, "light" "light source" and the like refer to any and all such lights, light sources, light guides and the like. Examples of such lights and light sources are discussed by way of example, in U.S. Pat. No. 5,521,392, which is hereby incorporated by reference for such disclosure.

However, with all of these modification, it was noticed that the area exposed directly to such a proper light would always cure first no matter how the light was generated and delivered to the curing surface, which may vary from standard, pulse, ramp to soft-start et al in terms of different curing modes.

It is known that how the materials cure often determines their ultimate performance including polymerization shrinkage, polymerization stress, and their mechanical properties. For restorative dental materials, additional properties like bonding strength, micro-leakage, micro-cracking and post-restoration sensitivity and the like, is believed to be associated with the curing process. Therefore, there has been much effort in the dental industry focussing on the development of new materials and new curing devices.

U.S. Pat. No. 4,385,344 discloses the use a halogen lamp that is filtered to supply light in the range of 400–700 nm. U.S. Pat. No. 5,290,169 discusses a light guide consisting of glass, acrylic, polycarbonate and polystyrene having a head with different concave surface geometry, a tapered section and a curved section to control total light output. U.S. Pat. No. 5,472,991 discloses to generate a light with different wavelengths during two step curing. U.S. Pat. No. 5,634,711 discusses a hand-held LED light with various light energy levels. U.S. Pat. No. 5,879,159 discloses a battery powered hand-held, high power ARC light for fast curing. U.S. Pat. No. 5,912,470 teaches to control total light output in a way to increase light intensity continuously or in stepped form. U.S. Pat. No. 5,975,895 discloses that to generate a series of light pulses at a predetermined frequency, a flash lamp was coupled to the trigger electronics. U.S. Pat. No. 6,008,264 discusses to generate a light with various power, wave form and modulation parameters. U.S. Pat. No. 6,033,223 discloses the use of a laser light and an optical fiber insert to initiate polymerization progressively from a portion thereof adjacent the bottom of the dental cavity towards a surface portion thereof. U.S. Pat. No. 6,079,861 discusses to control total light output from low to very high by two light sources. U.S. Pat. No. 5,229,230 teaches to enhance total incident light intensity on photo-sensitive surface by using new type of photomask with plurality of auxiliary patterns consist of transparent phase shit material spots. U.S. Pat. No. 5,468,577 discloses to increase total light intensity by using new type of photomask with plurality auxiliary patterns of small slots. U.S. Pat. No. 5,835,661 discusses to convert a point-like light into a collimated linear or planar light beam.

DISCLOSURE OF THE INVENTION

This invention relates to a method or technique to cure a polymerizable material with various light sources, particularly light curable materials that are selectively cured using special patterns. The patterns are either placed onto a special mask on the materials or onto the curing light tip, or by employing a special light source. As a result from such a segmental curing technique, the polymerization stress associated with the cured materials is limited or minimized due to extended molecular relaxation promoted by this controlled hybrid curing technique.

With this controlled segmental curing technique, heterogeneous curing zones of polymerization within a chemically homogenous material are created, from which a pre-gel-like behavior is demonstrated during the heterogeneous post-gel stage. The normal polymerization stress generated within those segments initially curing is relieved through stress relaxation within the partially cured or uncured segments adjacent to them. By such segmental stress relief, the severe final stress concentration occurring at the interface between the restorative material and the tooth structure can be avoided. As a result, the associated microleakage and microcracking is limited or minimized. Therefore, this technique can be understood as dividing the stress occurring over the entire composite/tooth interface into a series of incremental stresses over sub-interfaces (composite/composite) that prevents the overall polymerization stress from being transmitted to the composite/tooth interface and/or passed through the interface into the tooth structure. This unique feature is distinguished over other sequential curing techniques, such as soft-start curing, pulse curing, or the like.

An object of this invention is to provide a method by which the polymerizable materials could be selectively cured from the very first surface. As a result of such sectional curing, low polymerization shrinkage and especially low polymerization stress are expected with the cured materials. Because the polymerization stress associated with the cured section could get relief via its adjacent less cured section through normal relaxation.

In general, a method of curing a photo-polymerizable material with light energy from a light source, comprises the steps of exposing at least one selected segment of the material to the light energy while selectively limiting exposure of at least one substantially adjacent segment of the material to the light energy.

There is also provided according to the invention, a method of curing wherein said step of exposing a selected segment of the material to light energy while selectively limiting exposure of at least one substantially adjacent segment of the material to the light energy includes the steps of fitting the light source with a mask.

Another method, includes such curing wherein the mask has at least one first portion that is substantially transmissive of the spectrum of light required for curing the material.

A further such includes wherein the mask has at least one second portion which is non-transmissive of at least a portion of the spectrum of light required for curing the material.

A still further method includes wherein the second portion of said mask is substantially non-transmissive of the spectrum of light required to cure the material.

Another method includes wherein the steps of exposing at least one selected segment of the material to the light energy while selectively limiting exposure of at least one substantially adjacent segment of the material to the light energy, includes interposing a mask between the light source and the material.

An additional method includes wherein said step of selectively limiting exposure of a substantially adjacent segment of the material to the light energy includes preventing at least a portion of the light energy from reaching said adjacent segment.

A further method includes wherein said step of exposing a selected segment of the material to the light energy includes exposing a plurality of selected segments of the material to the light energy.

A still further method includes wherein said step of selectively limiting exposure of at least one substantially adjacent segment of the material to the light energy includes selectively limiting exposure of a plurality of adjacent segments of the material to the light energy.

Another method of curing a photo-polymerizable material comprises the steps of exposing at least one selected segment of the material to light energy while selectively limiting exposure of at least one substantially adjacent segment of the material to said light energy, wherein said step of exposing at least one selected segment of the material to said light energy includes directing light energy from a light source to said selected segment with a light guide comprising a plurality of light-transmitting fiber optic strands and a plurality of light-limiting strands, wherein said light-transmitting strands and said light limiting strands are arranged in a preselected pattern.

Another method of curing a photo-polymerizable material comprises the steps of exposing at least one selected segment of the material to light energy while selectively limiting exposure of at least one substantially adjacent segment of the material to said light energy, wherein said step of exposing at least one selected segment of the material to said light energy includes directing light energy from a plurality of solid state light-emitting devices, such as light emitting diodes, laser diodes or the like, toward the material, wherein said light emitting diodes are arranged in a preselected pattern such that said at least one adjacent segment of the material is not directly exposed to light.

A further method according to the invention for curing a photo-polymerizable material comprises the steps of exposing at least one selected segment of the material to light energy while selectively limiting exposure of at least one substantially adjacent segment of the material to said light energy, wherein said step of exposing at least one selected segment of the material to said light energy includes directing light energy from a plurality of solid state light-emitting devices such as light or laser light emitting diodes, toward the material, wherein at least one of said plurality of light emitting diodes can be selectively controlled to an on state such that it emits light energy, to an off state such that it does not emit light energy.

An additional method of curing a photo-polymerizable material comprises the steps of exposing at least one selected segment of the material to light energy while selectively limiting exposure of at least one substantially adjacent segment of the material to said light energy, wherein said step of exposing at least one selected segment of the material to said light energy includes directing light energy from a plurality of solid state light-emitting devices such as light emitting diodes, laser emitting diodes or the like, toward the material, wherein at least one of said plurality of light emitting diodes emits light of a different wavelength than at least one other of said plurality of light emitting diodes.

A method of reducing polymerization-induced stress in a photo-polymerizable material cured with light energy from a light source, comprises the steps of exposing at least one selected segment of the material to the light energy while selectively limiting exposure of at least one substantially adjacent segment of the material to the light energy.

A method of reducing the shrinkage rate of a photo-polymerizable material during curing of the material with light energy from a light source, comprises the steps of exposing at least one selected segment of the material to the light energy while selectively limiting exposure of at least one substantially adjacent segment of the material to the light energy.

A method of curing a photo-polymerizable material with light energy from a plurality of light sources, comprises the steps of exposing at least one selected segment of the material to the light energy while selectively limiting exposure of at least one substantially adjacent segment of the material to the light energy, by selectively controlling at least one of the plurality of light sources from an on state wherein light energy is emitted, to an off state wherein light energy is not emitted.

A method of curing a photo-polymerizable material with light energy from a plurality of light sources, comprises the steps of selectively exposing segments of the material to different light energy levels by controlling at least one of the plurality of light sources from an on state wherein light energy is emitted, to an off state wherein light energy is not emitted.

A method of curing a photo-polymerizable material with light energy from a plurality of light sources, comprises the steps of exposing different segments of the material to light energy in a preselected sequence by controlling at least one of the plurality of light sources from an on state wherein light energy is emitted, to an off state wherein light energy is not emitted.

A method of curing a photo-polymerizable material with light energy, comprises the steps of providing at least two light sources, each of said light sources emitting a different wavelength of light, and selectively exposing the material to light from said light sources. A further aspect of this method may be wherein a first segment of said material is first exposed to one of said plurality of light sources, followed by exposure to a second of said plurality of light sources having said different wavelength of light.

A light guide according to the invention for directing light to a photocurable material, comprises a mask to limit the transmission of light to a selected portion of the material.

A mask according to the present invention is interposed between the material to be cured and the light source, for use in curing the photocurable material, and comprises a mask pattern having at least one light limiting block, wherein said mask pattern block substantially prevents at least a portion of the light spectrum required to cure the material from directly reaching the surface of the material to be cured.

PREFERRED EMBODIMENTS FOR CARRYING OUT THE INVENTION

Although the present invention has application to any type of photocurable material, it will be exemplified by reference to light cured dental materials.

According to the present invention, the reduction in stress distribution within the material to be cured is provided. At the same time, there is achieved substantially complete and thorough cure throughout the material, which should actually increase the degree of conversion, which, in turn, increases the total amount of shrinkage. This typically has been viewed heretofore as a negative quality since increasing the overall shrinkage usually means more stress within the material when cured in the usual way. Another inventive property of the present invention is the ability to overcome the dilemma of wanting to allow for slow polymerization rates, thus allowing for reduction of stress build up through viscoelastic flow of the polymerizing materials before onset of gelation, while at the same time wanting to cure the materials rapidly to save time. Previously, this was only possible by using very low levels of light energy over longer periods of time. High-energy exposure of short duration can lead to rapid polymer development and potentially more stress. With the present invention invention, it is possible to cure rapidly while polymerizing slowly, thus overcoming a contradiction of principles.

To provide for the controlled segmental curing (or polymerization) according to the present invention, the light curable material or the tip of an otherwise conventional curing light guide (not shown) is covered with a special mask. Any suitable and otherwise conventional curing light mask is within the scope of the present invention. For example, the SPECTRUM, SPECTRUM 800, PROLIGHT and QHL 75 brand curing lights marketed by DENTSPLY International Inc., are useful in carrying out the present invention. The specific light chosen, its luminosity, wavelengths, filters or the like will be chosen based upon the nature the polymerizable material used, and not necessarily based upon the requirements of the present invention, unless otherwise noted. Another exemplary light useful in the practice of the present invention is shown in U.S. Pat. No. 4,385,344 which is hereby incorporated by reference for such disclosure.

Figure 1:
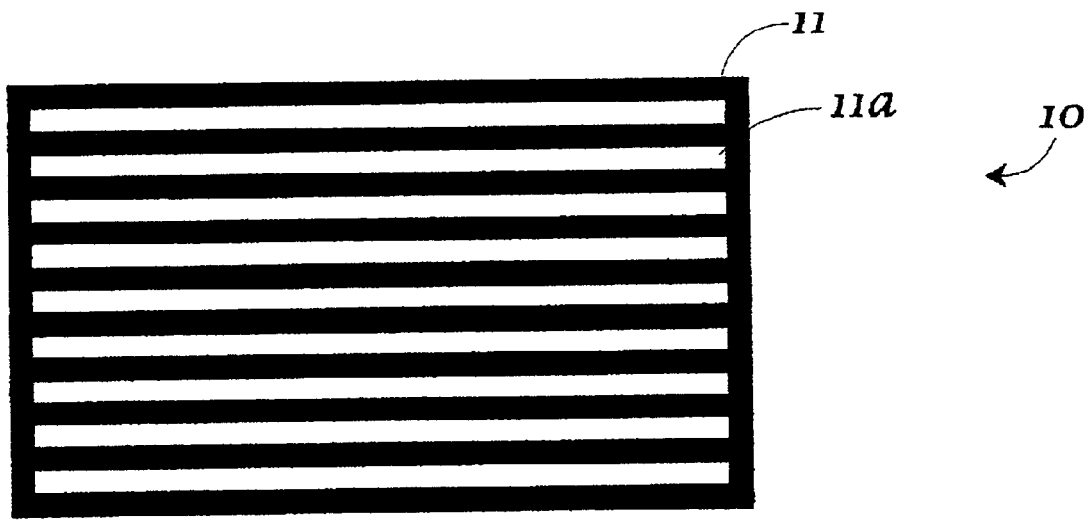
FIGS. 1–4 each show an exemplary embodiment of a mask having a mask pattern, either to placed upon a polymerizable material itself or onto a curing light, in order to effect the controlled segmental curing according to the present invention.
Figure 2:
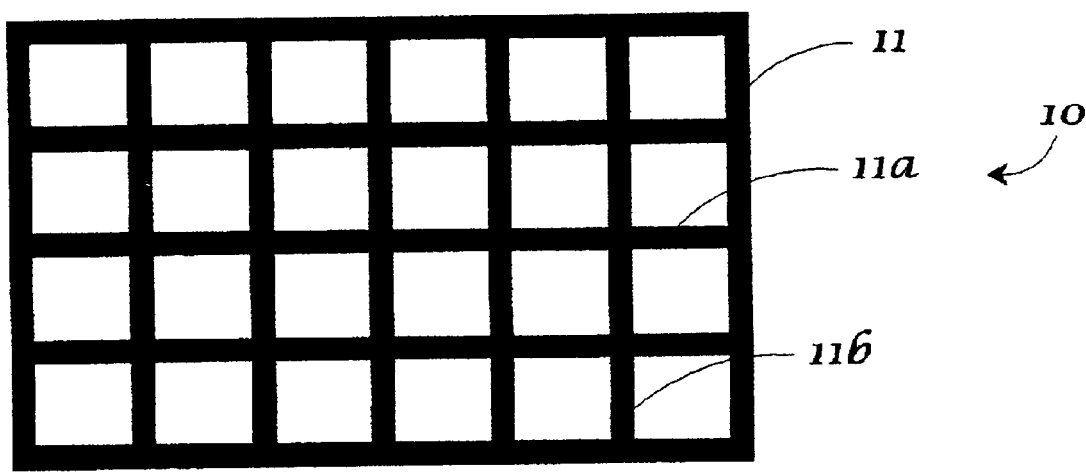
Figure 3:
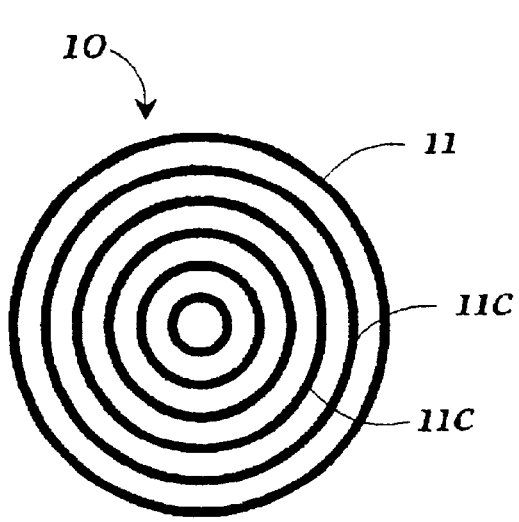
Figure 4:
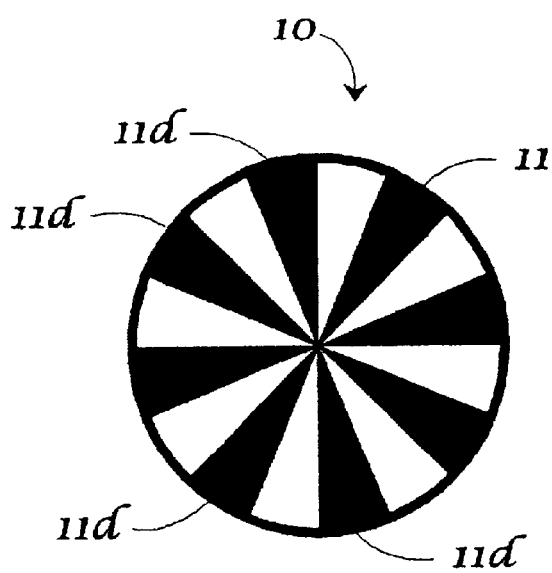

The invention provides a mask 10 having at least one and preferably a plurality of regularly or irregularly spaced mask segments 11. Exemplary mask 10 designs according to the present invention are shown in FIGS. 1–4. FIG. 1 shows a mask 10 comprised of a plurality of horizontal mask segments 11a; FIG. 2 shows a mask 10 having horizontal mask segments 11a and vertical mask segments 11b. FIG. 3 shows a mask 10 having concentric circle mask segments 11c. FIG. 4 shows a mask 10 having pinwheel mask segments 11d. These are exemplary only of the likely vast number of mask segment 11 designs possible. It is not possible to provide a drawing for the likely limitless number of such shapes, designs and patterns of masks 10 and associated mask segments 11. It is understood that all such shapes, patterns and designs fall within the scope of the present invention.

A mask 10 could be fabricated from, for example, plastics, metal or any substance that would not allow light transmission through mask segments 11. The mask 10 is used to prevent fully or partially prevent the material underneath the mask from curing. That is, when the photocurable material is exposed to light in an otherwise conventional manner, those portions of the material positioned adjacent to the mask segments 11 will not be exposed to the standard amount of light that the unmasked material is exposed to. Mask segments 11 preferably at least partially block transmission of light, and more preferably substantially completely block the transmission of light therethrough.

Figure 5:
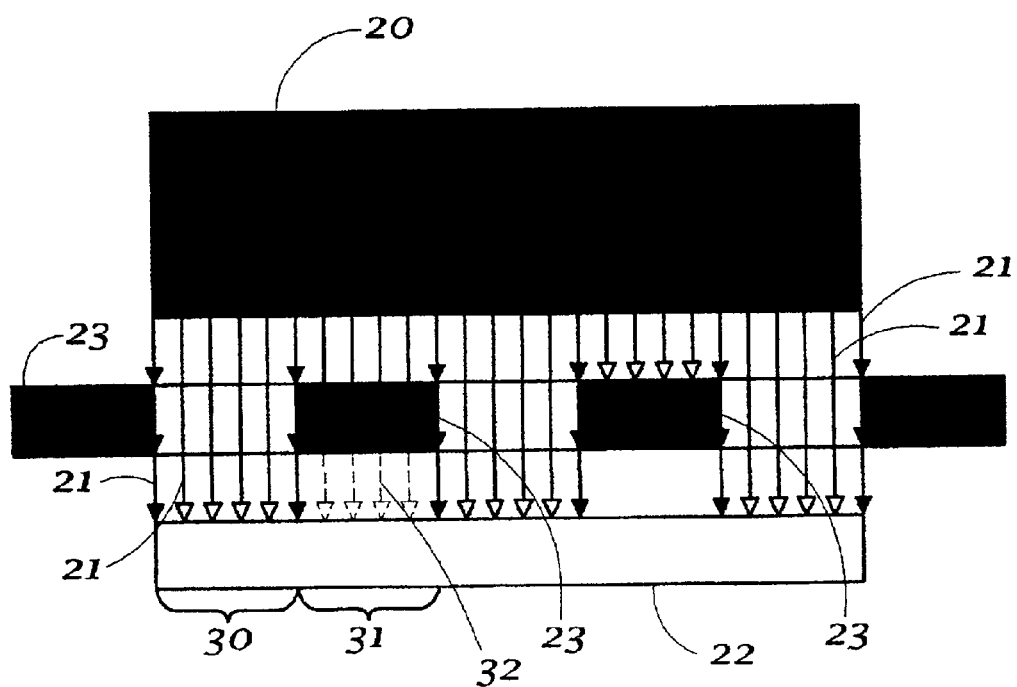
FIG. 5 is a partially schematic view of a light guide, mask and material to be cured, showing one method of the present invention.

A partially schematic representation of the use of a mask according to the invention is shown for example, in FIG. 5. In FIG. 5, a light guide 20 directs light energy represented by arrows 21, toward the surface of a material 22 to be cured. A mask represented by blocks 23 at least partially blocks the wavelength of light of light energy 21, or if desired, substantially all of light energy 21, from reaching material 22. Blocks 23 may pass light of only a selected wavelength, such that segments of material 22 receiving light energy 21 cure at different rates.

Similarly, if blocks 23 substantially block all light from reaching material 22, then again, segments of material 22 cure at different rates. It is also expected that adjacent areas of material 22 will cure sufficiently for the material's intended purpose by scatter into the adjacent segments. For example, in FIG. 5, a first set of segments 30 receive direct light energy 21, while a second set of segments 31 receive either no direct light energy 21, or they receive light energy of a different wavelength than light energy 21, as is represented by arrow 32. Light energy 21 and 32 may also represent different types of light energy, such as laser light, arc light or the like, or even different polarizations of light energy. By "adjacent" as used herein, it meant a segment such as segment 30, of the material to be cured that is contiguous with another segment 31 that receives either no direct light energy or light energy of a different wavelength, as was discussed hereinabove, such that the cure rate of one segment is different than the cure rate of an adjacent segment.

Figure 6:
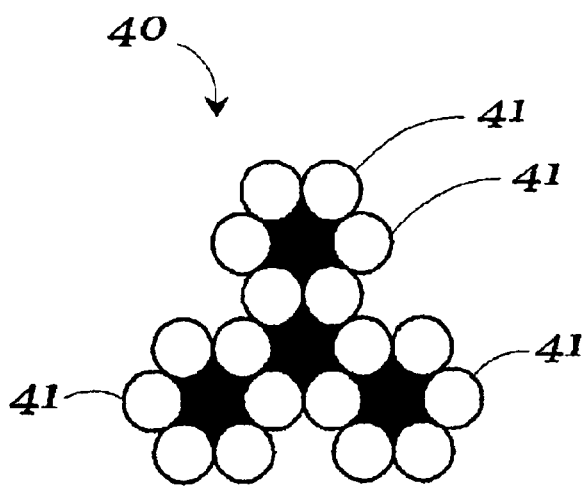
FIG. 6 is a front view of a fiber optic light guide according to the invention.
Figure 7:
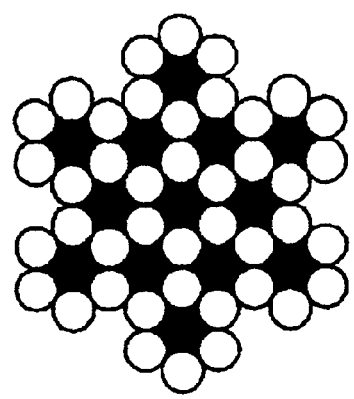
FIG. 7 is another embodiment of the light guide of FIG. 6.

As depicted in FIG. 6, another type of light may be provided with a light guide 40 having a plurality of fiber optic strands 41, as is known in the art of light guides. Strands 41 convey light in the known manner. In order to create a segmental cure pattern upon a dental material, strands 41 may be positioned together with blocking strands 42. Blocking strands 42 may be non-transmissive of light, or they may be transmissive of a different wavelength of light as compared to strands 41. Light from light guide 40 is conveyed to the material to be cured in the manner as described above with reference to FIG. 5. Any pattern of strand arrangement is within the scope of the invention, and as with other means of masking or providing different cure segments described herein, will vary depending upon the actual material to be cured and its inherent characteristics. Another pattern for light guide 40 is shown for example, in FIG. 7.

Figure 8:
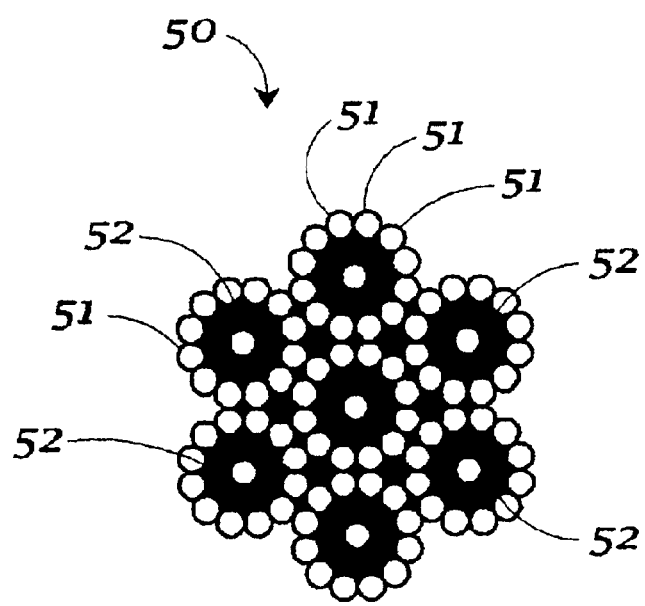
FIG. 8 is an arrangement of solid state light emitting devices according to the invention.

FIG. 8 depicts a solid state, light emitting device arrangement 50, having for example, a number of light emitting diodes 51 and 52. By solid state light emitting device, it is intended to mean an otherwise conventional light or laser light emitting diode or the like. Diodes 51 and 52 can be turned on such that light of a proper wavelength to cure a photopolymerizable is emitted. Alternatively, light from certain diodes, such as diodes 51 can be turned on, while diodes 52 are turned off, or vice versa. Another alternative according to the invention is to provide diodes 51 emitting a certain wavelength of light while diodes 52 emit a different wavelength of light. All such variations provide for segmental curing according to the invention. It is also within the scope of the invention to alternately turn diodes 51 and 52 on or off during curing, either randomly or according to a preselected pattern. As with all of the variations of the present invention, including the other masks, light guides or the like discussed herein, the material to be cured can also be moved such that different segments of the material are exposed to different light energies, or no light energies, at different times. Thus, one segment of the material receives light energy of a predetermined wavelength, while at least one other segment of the material receives a limited exposure to light energy. By "limited" it is meant either no direct light energy to the segment surface or that it receives light energy of a different wavelength. Of course, the light sources or guides according to the invention may use multiple masks such that light from the sources is filtered throughout the entire material exposure area. It is also contemplated that different cure rates can be effected in the material by changing the filtering aspects of the mask of type of light source or light guide provided.

Depending upon the nature of mask 10, or other light or light guide as described herein, the material underneath could be partially polymerized due to light scattering. The resulting difference in polymerization rate within the material makes it possible to control polymerization stress. Therefore, this technique is referred to as a "controlled segmental curing". In addition to using a mask 10, similar curing light patterns can also be realized by using a specially designed light, for example, linear polarized light, which allows only light transmission in one direction. Alternatively it is possible to incorporate a pattern generator such as light emitting diodes 50, within the light guide such that the light pattern emitted can act as a special mask. Of course, the mask, a special light source and a special light guide pattern generator, in combination with continuous intensity and/or varying generation frequency or varying the energy level of the emitted light, could also be used to control polymerization stress.

As stated above, any light cured material is within the scope of the present invention. Exemplary such materials include dental materials, such as composites, cements or the like. Commercially available products include those from DENTSPLY such as ESTHET-X, TPH, APH, CALIBRA, PRIME & BOND NT and FLUORCORE brand dental materials. These materials and others, all of which are useful in the practice of the present invention, may be variably cured with actinic light, visible light, laser light, ultraviolet light, and the like. Exemplary photocurable dental materials are also disclosed in U.S. Pat. Nos. 4,514,174 and 4,491,453, which are hereby incorporated by reference for such disclosure.

The chemical composition, molecular weight, and associated chemical and physical entanglement of the materials determine the mechanical properties of linear or cross-linked polymers. Molecular weight or chain growth is highly dependent on the polymerization rate and reaction kinetics. For any in-situ polymerization, the polymerization rate and kinetics would affect the physical and mechanical property as well. In direct polymerization of a cross-linkable system, in which permanent chemical entanglement is made possible, the cured material offers excellent physical and mechanical properties in a very short polymerization time. However some physical property trade-off occurs. Polymerization stress build-up in a cross-linked system becomes more severe than a similar linear counterpart. Such a stress build-up can result in disastrous properties in certain application of this quick, easily cross-linked material. In a typical cross-linked dental restorative composite, for example, the accumulated polymerization stress can pass trough the well-bonded composite/tooth interface into the tooth structure, eventually causing the tooth to crack. Such a stress transfer can also break any weak bonding area and lead to microleakage. Both cases result in failed dental restorations.

According to the present invention, one mass of chemically homogenous material is exposed to a heterogeneous light source due to the presence of the mask 10, which provides a heterogeneous curing rate throughout the material and enables stress relaxation and overall reduction of stress build-up. This approach will lead to a more successful dental restoration than with previous techniques.

Therefore, according to the present invention, photopolymerization in selected areas, segments or sections, leading to a slower shrinkage rate and hence, lower polymerization stress, can be accomplished by techniques including the following:

1. Using a photomask consisting of various predetermined patterns, which allow the curing light selectively pass through it, then the materials underneath would be polymerized in a sequence way.
2. Using a predetermined pattern to rearrange the light guide, which is composed by a bunch of glass fiber and carbon fiber or other fibers with limited light transmit capability. Obviously, without the photomask mentioned above, the direct contacted materials with such a special curing tips would polymerize in different rate.

3. Using special optical filter such as polarizer, the incident light transmission behavior enables the polymerizable materials cure in controlled direction.

The polymerizable materials could be reformulated in a composition which allow the materials to exhibit different responses to different lights, which include different polymerizable groups attached in same bifunctional polymerizable molecules; or different supermolecular clusters. Within the material there may be at least two different photoinitiating materials, each active to different wavelengths of light. Different light initiators may be employed in the material itself, such that exposure to different lights or even to the same light causes segmental curing according to the invention. In the dental industry, it is known to use initiators responsive to using CQ at about 475 nm and one using PPA at about 420 nm. It is also within the scope of the invention to combine for example, visible and UV initiators, which are themselves known in the art, but are used according to the invention with a "switchable" light source between two wavelength regions while curing.

In sum, the unique feature associated with such a sequential curing as demonstrated by the mask curing and other of the inventive techniques is to enable the polymerization stress relief to occur even during the macroscopically post-gel stage, because of the nature of its microscopically heterogeneity polymerization

EXAMPLES

A photocurable composite dental restorative material can be tested using a 60/30 mode and a 10/10 mode for comparison, and tested for shrinkage using an ADA mercury dilatometer. A "60/30" mode test subjects the test material to a curing light for 60 seconds, followed by an hour rest period to allow heat dissipation, and then followed by an additional 30 exposure to the curing light. A "10/10" mode test is similar except each exposure is for 10 seconds. Test materials can be placed upon a glass slide with a mask on the opposite side of the slide, or by using one of the other exposure techniques according to the invention and as above described.

It is common with a 60/30 mode test on a masked glass slide for a composite dental material to exhibit an increasing shrinkage rate of about 6 to about 17% by area. Even with the lower curing intensity in the 10/10 mode test, the composite material cured on the masked glass slide will exhibit an increasing shrinkage of from about 7 to about 13% by area. Such an increase in shrinkage indicates a slower polymerization rate than that of the unmasked cured material. A slower polymerization rate indicates a lower polymerization stress accumulation within the cured composite material. It might be argued that lower intensity in mask slide cases might lead to slower polymerization and higher shrinkage. However, this is not the direct reason as was confirmed by the fact that total intensity as in the 10/10 mode test will not necessarily generate lower shrinkage than that generated by the 60/30 mode test.

Various mask patterns were explored to study their effect on the curing behavior as measured by shrinkage, stress, and mechanical properties. Typically, parallel, cross, circle, and/or fan-like or any other irregular patterns can be used as masks, either directly on the materials or directly onto the tip of curing light probe, or by the arranged patterns of the solid state light emitting diodes, polaraized light sources, light guides and other devices according to the invention and as described hereinabove. As was discussed, it is envisioned for example, that a special light guide could be use containing the regular glass fibers with additional, non-light transmitting fibers, such as black carbon fibers or other filaments, in a specific arrangement to form a particular pattern. Other controlled, segmental curing may also be realized by using special light pattern generators and/or using specially oriented light, for example, linear polarized light. Materials used for the testing as described in this disclosure included testing photopolymerizable materials as were above described.

1. Step Curing Effect on Polymerization Shrinkage/Stress:
   After a short initial curing circle (1 second), a delay of 6 minutes was elapsed, followed by a $2^{nd}$ irradiation of various times ranging from 1, 9, 19, 29, 59 seconds, respectively. It was found that the total shrinkage with such a "step cure" sequence was lower than the same total cure time proceeding a single continuous exposure. This result demonstrated that once partially cured (1 second) the material still developed a network that had reduced mobility in subsequent curing steps, leading to reduction in overall stress build-up.

2. Under various initiation cure times, different shrinkage and stress were generated. In particular, increasing stress was indirectly revealed by the onset "pop-off" time from a typical shrinkage measurement. That is, as stress resulting from polymerization increased, the sample being cured on a glass plate would lift or "pop-off" its glass substrate. Different materials exhibit different adhesion to the standard glass slide used in the shrinkage test. With increased accumulation of polymerization stress, different pop-off times were observed.

3. By applying a mask to the glass slide (either parallel lines or crossed lines) in same shrinkage test, it was found that for the same material, the "pop-off" time was significantly delayed or eliminated. This demonstrated that stress generation was limited or minimized, and was not strong enough to break its bond with the glass substrate. Typically for TPH Spectrum, the "pop-off" time is about 6–9 seconds on a standard glass slide; but it is increased more than two-fold to 15 seconds on a masked glass slide.

4. Since no significant density difference occurred between the materials cured on a standard glass slide and on a masked glass slide after 24 hrs, it is expected their mechanical properties and overall shrinkage should be same or at least similar to each other. Therefore stress reduction occurred despite the same amount of overall shrinkage of the material.

Based upon the foregoing disclosure, it should now be apparent that the method of light curing materials as described herein will carry out the objects of the invention set forth hereinabove. It is, therefore, to be understood that any obvious variations fall within the scope of the claimed invention and thus, the selection of specific constituents and substituents can be determined without departing from the spirit of the invention herein disclosed and described. Thus, the scope of the invention shall include all modifications and variations that may fall within the scope of the attached claims.

What we claim is:

1. A method of curing a photo-polymerizable composite dental material to form a dental restoration of a tooth, using light energy from a light source, wherein prior to polymerization the composite dental material is placed in physical contact with a tooth to be restored, such that a composite-to-tooth interface is established, comprising the steps of:

exposing at least one selected segment of the material to the light energy while selectively limiting exposure of at least one substantially adjacent segment of the material to the light energy;

wherein said step of exposing a selected segment of the material to light energy while selectively limiting exposure of a least one substantially adjacent segment of the material to the light energy includes the steps of fitting the light source with a mask; wherein said mask has at least one first portion that is substantially transmissive of the spectrum of light required for curing the material, and at least one second portion which is non-transmissive of at least a portion of the spectrum of light required for curing the material;

such that the stress occurring over the entire composite-to-tooth interface is effectively divided into a series of incremental stresses over composite-to-composite sub-interfaces, thereby substantially preventing the overall polymerization stress from being transmitted to the composite-to-tooth interface or being passed through the interface into the tooth structure.

* * * * *